US010485259B2

(12) United States Patent
Challakere

(10) Patent No.: US 10,485,259 B2
(45) Date of Patent: Nov. 26, 2019

(54) SYNTHETIC AVIAN-FREE EGG WHITE SUBSTITUTE AND METHOD OF MAKING SAME

(71) Applicant: Kedarnath Krishnamurthy Challakere, Santa Clara, CA (US)

(72) Inventor: Kedarnath Krishnamurthy Challakere, Santa Clara, CA (US)

(*) Notice: Subject to any disclaimer, the term of this patent is extended or adjusted under 35 U.S.C. 154(b) by 69 days.

(21) Appl. No.: 15/562,183

(22) PCT Filed: Mar. 28, 2016

(86) PCT No.: PCT/US2016/024430
§ 371 (c)(1),
(2) Date: Sep. 27, 2017

(87) PCT Pub. No.: WO2016/160655
PCT Pub. Date: Oct. 6, 2016

(65) Prior Publication Data
US 2018/0084814 A1    Mar. 29, 2018

Related U.S. Application Data

(60) Provisional application No. 62/169,128, filed on Jun. 1, 2015, provisional application No. 62/139,492, filed on Mar. 27, 2015.

(51) Int. Cl.
*A23L 33/17* (2016.01)
*C07K 14/79* (2006.01)
*C12N 15/81* (2006.01)
*A23L 31/10* (2016.01)
*C07K 14/465* (2006.01)
*C12P 21/02* (2006.01)

(52) U.S. Cl.
CPC .............. *A23L 33/17* (2016.08); *A23L 31/10* (2016.08); *C07K 14/465* (2013.01); *C07K 14/79* (2013.01); *C12N 15/815* (2013.01); *C12P 21/02* (2013.01); *A23V 2002/00* (2013.01)

(58) Field of Classification Search
CPC ....... A23L 33/17; A23L 31/10; C07K 14/465; C07K 14/79; C12N 15/815; C12P 21/02; A23V 2002/00
See application file for complete search history.

(56) References Cited

U.S. PATENT DOCUMENTS

| 2003/0059873 | A1* | 3/2003 | Meng ............. C07K 14/005 435/69.1 |
| 2003/0172387 | A1* | 9/2003 | Zhu ............... A01K 67/0275 800/6 |
| 2008/0120732 | A1* | 5/2008 | Elliot ............ C07K 16/2896 800/4 |
| 2009/0133134 | A1* | 5/2009 | Wang ............. A01K 67/0275 800/4 |
| 2009/0165155 | A1* | 6/2009 | Zhu ............... A01K 67/0275 800/19 |
| 2011/0301249 | A1 | 12/2011 | Challakere |
| 2013/0084361 | A1 | 4/2013 | Shepheard |

FOREIGN PATENT DOCUMENTS

WO    WO-2010068897 A2    6/2010
WO    WO-2013148330 A1    10/2013

OTHER PUBLICATIONS

International Search Report and Written Opinion for PCT/US16/24430, dated Jul. 1, 2016.
International Preliminary Report on Patentability for PCT/US16/24430, dated Oct. 12, 2017.
Ramat, "Protein Purification Using Expanded Bed Chromatography", Master of Science Thesis, 2004, Chemical Engineering Department, Worcester Polytechnic Institute, pp. 1-87.
Gene Sequence for TF transferrin (ovotransferrin) [ *Gallus gallus* (chicken) ] Gene ID: 396241. Available from: <https://www.ncbi.nlm.nih.gov/gene/396241>.
Gene Sequence for Chicken mRNA for ovotransferrin (conalbumin) GenBank: X02009.1. Available at: https://www.ncbi.nlm.nih.gov/nuccore/X02009.1.

\* cited by examiner

*Primary Examiner* — Anthony J Weier
(74) *Attorney, Agent, or Firm* — Winstead PC

(57) ABSTRACT

In some embodiments, the present disclosure relates to an avian-free egg white composition including 45-63% Ovalbumin, 9-15% Ovotransferrin, 0-15% Ovomucoid, 3-5% Ovoglobulin G2, 3-5% Ovoglobulin G3, 2.5-5% Ovomucin, 3-5% Lysozyme, 1-2% Ovoinhibitor, 0.8-1.5% Ovoglycoprotein, 0.6-1.0% Flavoprotein, 0.3-0.8% Ovomacroglobulin, 0.02-0.1% Avidin, and 0.02-0.1% Cystatin. In some embodiments, the composition includes an edible yeast and one or more of the preceding proteins. In some embodiments, the avian-free egg white further includes one or more of: flavor enhancers, calcium supplements, added vitamins, and a gelling agent. In some embodiments, the present disclosure pertains to a non-allergenic egg-white composition for human consumption. In some embodiments, the present disclosure pertains to methods of making the avian-free egg-white composition.

22 Claims, No Drawings

US 10,485,259 B2

SYNTHETIC AVIAN-FREE EGG WHITE SUBSTITUTE AND METHOD OF MAKING SAME

CROSS-REFERENCES TO RELATED APPLICATIONS

This application claims the benefit under 35 U.S.C. § 119(e) of U.S. Provisional Patent Application No. 62/139,492, filed Mar. 27, 2015, and U.S. Provisional Patent Application No. 62/169,128, filed Jun. 1, 2015, each of which is incorporated herein by reference in its entirety as if fully set forth herein.

TECHNICAL FIELD OF THE INVENTION

The present invention relates to synthetic egg white and egg white products, such as an egg patty, which comprises all of the proteins present in an egg white, but which does not contain unhealthy yolk or yolk components, such as cholesterol. The present invention also relates to processes for making the synthetic egg white and egg white products.

BACKGROUND OF THE INVENTION

Both the white and yolk of an egg are rich in nutrients (e.g., proteins, vitamins and minerals), with the yolk also containing cholesterol, fat soluble vitamins, and essential fatty acids. Eggs are a very good source of inexpensive, high quality protein. More than half the protein of an egg is found in the egg white along with vitamin B2 and lower amounts of fat and cholesterol than the yolk. The whites are rich sources of selenium, vitamin D, B6, B12 and minerals such as zinc, iron and copper. Egg yolks contain more calories and fat. They are the source of cholesterol, fat soluble vitamins A, D, E and K and lecithin.

However, it is well known that some characteristics of egg and egg products are often cause for concern, and otherwise impede the ability for some people to consume food products having egg products therein. For example, many individuals may be unable to, or would prefer not to consume egg products due to health issues like egg allergies or high cholesterol. Other concerns with consuming egg are associated with culinary preferences (such as, a vegetarian or vegan diet), use of antibiotics and hormones during poultry production, and diseases associated with poultry (such as, for example, bird flu). Additionally, the high cost and/or cost fluctuations in the price of eggs and the contamination of salmonella carried by eggs have also been a concern of food manufacturers. Therefore, there is a need in the art to reduce or eliminate the content of egg and/or egg-based products in some food products to address these concerns.

SUMMARY OF THE INVENTION

In some embodiments, a synthetic avian-free egg white composition comprises: 45-63% Ovalbumin, 9-15% Ovotransferrin, 3-5% Ovoglobulin G2, 3-5% Ovoglobulin G3, 2.5-5% Ovomucin, 3-5% Lysozyme, 1-2% Ovoinhibitor, 0.8-1.5% Ovoglycoprotein, 0.6-1.0% Flavoprotein, 0.3-0.8% Ovomacroglobulin, 0.02-0.1% Avidin, and 0.02-0.1% Cystatin. In some embodiments, the avian-free egg white composition comprises: 45-63% Ovalbumin, 9-15% Ovotransferrin, 0-15% Ovomucoid, 3-5% Ovoglobulin G2, 3-5% Ovoglobulin G3, 2.5-5% Ovomucin, 3-5% Lysozyme, 1-2% Ovoinhibitor, 0.8-1.5% Ovoglycoprotein, 0.6-1.0% Flavoprotein, 0.3-0.8% Ovomacroglobulin, 0.02-0.1% Avidin, and 0.02-0.1% Cystatin. In some embodiments, one or more proteins may be omitted to create a specified, desired product.

In some embodiments, the avian-free egg white further comprises flavor enhancers. In some embodiments, yeast or modified yeast may be used to enhance flavor and/or texture of a product. In some embodiments, the avian-free egg white further comprises calcium supplement. In some embodiments, the avian-free egg-white composition comprises added vitamins. In some embodiments, the avian-free egg-white composition further comprises a gelling agent. In some embodiments, the aforementioned composition comprises algal omega-3 fatty acids. In some embodiments, such a composition does not induce an allergic reaction upon ingestion by a subject.

In some embodiments, the present disclosure pertains to a method of making an avian-free egg white substitute comprising expressing each of the aforementioned proteins individually in a genetically modified organism. In some embodiments the genetically modified organism is a yeast species. In some embodiments, the yeast may be *Sacchromyces cervevisiae*. In an embodiment, the yeast may be *Picchia pastoris*. In some embodiments, the method comprises expressing at least one of the aforementioned proteins in bacteria. In some embodiments the bacteria is *E. coli*. Since Ovomucoid is suspected to cause the majority of human allergies, the formulation may substitute Ovomucoid with either a gelling agent such as pectin or a different serine protease inhibitor which may or may not be a protein (i.e., may be a metal). Albumin, which comprises 54% of egg white components, may be produced either via genetically engineered organisms or via alternate synthetic pathways. In an embodiment of the present disclosure, the method further comprises, expanding the genetically modified cells expressing each of the aforementioned proteins in bioreactors. In some embodiments, the method comprises harvesting and purifying the expressed proteins.

In some embodiments, the present disclosure pertains to a method of making a protein enhanced nutritional yeast. In some embodiments, genes for a plurality of the aforementioned proteins may be expressed in at least one yeast organism. In an embodiment, genes for at least one of the afore-mentioned protein are expressed in a plurality of yeast. In an embodiment, the method comprises combining the colonies of the yeast expressing different proteins in proportions to create the desired edible product. In an embodiment, this method requires least amounts of cellular energy for transcription.

In some embodiments, the method comprises expressing at least one gene encoding a protein selected from the group comprising: Ovalbumin, Ovotransferrin, Ovomucoid, Ovoglobulin G2, Ovoglobulin G3, Ovomucin, Lysozyme, Ovoinhibitor, Ovoglycoprotein, Flavoprotein, Ovomacroglobulin, Avidin, and Cystatin in at least one yeast organism. In an embodiment, the method comprises combining yeast colonies and individually expressing at least one of the aforementioned proteins in proportions similar to proportions for each protein found in natural egg-white to form protein-enhanced nutritional yeast. In an embodiment, this method requires the least amounts of cellular energy for transcription.

DETAILED DESCRIPTION OF THE INVENTION

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Unless defined otherwise, all technical and scientific terms used herein have the meaning commonly understood by a person skilled in the art to which the invention belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th ed., R. Reigers et al. (eds.), Springer Verlag (1991); and Hale & Marham, The Harper Collins Dictionary of Biology (1991).

The following definitions are set forth to illustrate and define the meaning and scope of the various terms used to describe the invention herein.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to translational start and stop codons, promoter sequences, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eucaryotic cells are promoters, polyadenylation signals, and enhancers. All of these control sequences need not be present in a recombinant vector so long as those necessary and sufficient for the transcription and translation of the desired gene are present.

The vector may be any vector which may conveniently be subjected to recombinant DNA procedures, and the choice of vector will often depend on the host cell into which it is to be introduced. Thus, the vector may be an autonomously replicating vector, i.e., a vector which exists as an extra chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The vector is preferably an expression vector in which the encoding DNA sequence is operably linked to additional segments required for transcription of the DNA. In general, the expression vector is derived from plasmid or viral DNA, or may contain elements of both. The vector may further comprise elements, such as, for example, polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention. "Exogenous gene" or "exogenous coding sequence" refers to a nucleic acid sequence not naturally present in a particular tissue or cell.

"Exogenous protein" refers to a protein not naturally present in a particular tissue or cell.

"Endogenous gene" refers to a naturally occurring gene or fragment thereof normally associated with a particular cell.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro, or in vivo, the latter being performed by a host cell through posttranslational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

Eggs are an important source of nutrition. Since the domestication of the chicken, people have been enjoying and nourishing themselves with eggs. Additionally, eggs are an important and versatile ingredient for cooking, as their particular chemical makeup is literally the glue of many important baking reactions. Egg and egg protein based products are essential ingredients for the volume, texture, and shelf life of aerated food products such as muffins, cakes, cookies, breads, and various other baked products. Egg and egg protein based products are also used as ingredients in non-aerated food products such as noodles, pastas, dumplings and similar foods to provide the hardness and elasticity characteristics of these products, typically to enhance the cooking stability and shelf-life of these products. Other benefits to the use of egg and egg protein based products include providing smoother dough, where applicable, and providing improved processing tolerances for industrial scale cooking situations.

However, natural fresh whole poultry eggs are known to be high in triglycerides, high density lipids, and, particularly, cholesterol. Because of these components and their adverse effects on the human cardiovascular system, persons at high risk of cardiovascular disease have a continuing need for careful dietary control of the types of foods consumed. Additionally, natural fresh whole poultry eggs are known to be prone to bacterial contamination and have been implicated in many cases of food poisoning. Pasteurization of natural eggs has simply not been an available solution to the problem since such process treatments of natural whole poultry eggs serve to break down the white of the egg, causing it to become thin and runny, and causing the egg to appear old rather than fresh.

Thus, despite egg being labeled as a good source of nutrition, many people may need to avoid consumption of natural eggs or egg-related products due to religious reasons, for e.g. vegetarians. Individuals may also not be able to consume eggs or egg-containing products due to health reasons, for e.g., allergies to eggs or egg-containing products. Egg is one of the most common causes of food allergy. It is estimated that most children outgrow egg allergy by the age of five, but some people remain allergic for a lifetime. The egg is made up of many different proteins, some of which are allergenic and others which are not. Most people with an egg allergy are allergic to the egg white proteins, and others are allergic to the yolk.

As a consequence of the foregoing problems and the increasing awareness thereof by the consuming public, there exists a need for a synthetic egg-white composition that is nutritionally at par, if not better, with natural egg, without components that are known to adversely affect cardiovascular health. Additionally, there is a need for synthetic egg-white composition that is avian-free and appeals to vegetarians, because it is animal free.

Egg white is the common name for the clear liquid (also called the albumen or the glair/glaire) contained within an egg. In chickens it is formed from the layers of secretions of the anterior section of the hen's oviduct during the passage of the egg. It forms around either fertilized or unfertilized egg yolks. The primary natural purpose of egg white is to protect the yolk and provide additional nutrition for the growth of the embryo (when fertilized). Egg white consists primarily of about 90% water into which is dissolved 10% proteins. Chicken egg white is about two-thirds of an egg's total weight out of its shell, with nearly 92% of that weight coming from water. The remaining weight of the egg white comes from protein, trace minerals, fatty material, vitamins, and glucose. A raw U.S. large egg white weighs 33 grams with 3.6 grams of protein, 0.24 grams of carbohydrate and 55 milligrams of sodium. It also contains about 17 calories and no cholesterol. Egg white is an alkaline solution and contains approximately 40 different proteins. The egg white proteins by percentage, along with their natural functions are: 54% Ovalbumin (Nutrition); 12% Ovotransferrin (Binds iron), 11% Ovomucoid (Blocks digestive enzymes), 4% Ovoglobulin G2, 4% Ovoglobulin G3, 3.5% Ovomucin, 3.4% Lysozyme (Kills bacteria), 1.5% Ovoinhibitor, 1% Ovoglycoprotein, 0.8% Flavoprotein, 0.5% Ovomacroglobulin, 0.05% Avidin (Binds biotin), and 0.05% Cystatin.

Unlike the yolk, which is high in lipids (fats), egg white contains almost no fat, and carbohydrate content is less than 1%. Egg whites contain just over 50% of the protein in the egg. Egg white proteins have become an important and desirable ingredient to the food industry due to their functional properties which include gelling, foaming, and emulsification. Egg white is also well recognized as an excellent source of nutrition. Additionally, egg white is also a component of certain vaccines, for e.g., influenza vaccine.

In some embodiments, the present disclosure relates to an avian-free egg white composition comprising 54% Ovalbumin, 12% Ovotransferrin, 11% Ovomucoid, 4% Ovoglobulin G2, 4% Ovoglobulin G3, 3.5% Ovomucin, 3.4% Lysozyme, 1.5% Ovoinhibitor, 1% Ovoglycoprotein, 0.8% Flavoprotein, 0.5% Ovomacroglobulin, 0.05% Avidin, and 0.05% Cystatin. In some embodiments, the composition further comprises flavoring agents. In some embodiments, the avian-free egg white further comprises calcium supplement. In some embodiments, the avian-free egg-white comprises vitamins. In some embodiments, the avian-free egg-white composition further comprises a gelling agent. In some embodiments, the compositions disclosed herein further comprise additives. In some embodiments, the additives comprise flavoring agents, metals, protease inhibitors, pectins, vitamins, calcium, magnesium, iron, plant-derived omega-3 fatty acids, and supplements.

In some embodiments, the present disclosure pertains to a method of making an avian-free egg white substitute comprising expressing each of the aforementioned proteins individually in a genetically modified organism. In some embodiments the genetically modified organism is a yeast species. In some embodiments of the present disclosure, microorganisms are used for making the recombinant proteins that comprise the synthetic avian-free egg white composition. In some embodiments, the microorganisms comprise, but are not limited to, *Saccharomyeces Cerevesiae, Picchia Pastoris, Escherichia Coli*, and blue-green algae. In some embodiments, the compositions disclosed herein further comprise additives. In some embodiments, the additives comprise flavoring agents, metals, protease inhibitors, pectins, vitamins, calcium, magnesium, iron, plant-derived omega-3 fatty acids, and supplements.

In some embodiments, the method comprises expressing at least one of the aforementioned proteins in bacteria. Some embodiments the bacteria is *E. Coli*. Since Ovomucoid is suspected to cause the majority of human allergies, the formulation may substitute Ovomucoid with either a gelling agent such as pectin or a different serine protease inhibitor which may or may not be a protein (i.e., may be a metal). Albumin, which comprises 54% of egg white components, may be produced either via genetically engineered organisms or via alternate synthetic pathways. In an embodiment of the present disclosure, the method further comprises, expanding the genetically modified cells in bioreactors. In some embodiment, the method furthermore comprises harvesting and purifying the expressed protein. In some embodiments, the method further comprises mixing the individual proteins in proportions similar to the proportions found in natural egg-white composition to form an avian-free egg white type compound.

In some embodiments, the present disclosure pertains to a method of making a protein enhanced nutritional yeast. In some embodiments, the method comprises expressing at least one gene encoding a protein selected from the group comprising: Ovalbumin, Ovotransferrin, Ovomucoid, Ovoglobulin G2, Ovoglobulin G3, Ovomucin, Lysozyme, Ovoinhibitor, Ovoglycoprotein, Flavoprotein, Ovomacroglobulin, Avidin, and Cystatin in at least one yeast organism. In an embodiment, the method comprises combining yeast colonies and individually expressing at least one of the aforementioned proteins to form protein-enhanced nutritional yeast. In an embodiment, this method requires the least amounts of cellular energy for transcription. In some embodiments, the protein enhanced nutritional yeast comprises edible yeast and one or more of the following proteins: 45-63% Ovalbumin, 9-15% Ovotransferrin, 0-15% Ovomucoid, 3-5% Ovoglobulin G2, 3-5% Ovoglobulin G3, 2.5-5% Ovomucin, 3-5% Lysozyme, 1-2% Ovoinhibitor, 0.8-1.5% Ovoglycoprotein, 0.6-1.0% Flavoprotein, 0.3-0.8% Ovomacroglobulin, 0.02-0.1% Avidin, and 0.02-0.1% Cystatin.

In some embodiments, the present disclosure pertains to a method of making recombinant edible protein compositions for human and animal consumption. In some embodiments, the recombinant edible protein composition comprises egg-white proteins. In an embodiment, the method comprises providing at least one vector comprising a gene encoding at least one protein selected from the group comprising: Ovalbumin, Ovotransferrin, Ovomucoid, Ovoglobulin G2, Ovoglobulin G3, Ovomucin, Lysozyme, Ovoinhibitor, Ovoglycoprotein, Flavoprotein, Ovomacroglobulin, Avidin, and Cystatin. In some embodiments, the vector is a viral vector. In some embodiments, the method further comprises providing at least one host cell(s). In some embodiments the host cell(s) is a bacterial cell. In some embodiments, the host cell(s) is a yeast cell. In some embodiments, the method comprises transforming, transfecting, or infecting the at least one host cell(s) with the aforementioned vector comprising a gene encoding at least one protein. In some embodiments, the method comprises a plurality of host cells each transfected, transformed, or infected with a vector encoding at least one protein such that each protein is a different protein. In some embodiments, the method further comprises providing media to culture the transformed, transfected, or infected host cell(s). In some embodiments, the method comprises culturing the transformed or transfected or infected host cell(s) in the culture media under conditions sufficient to express the at least one protein. In some embodiments, the method comprises the step of purifying the at least one protein. Purification of the crude protein may be achieved using any method known in the art, including, without limitation, affinity chromatography. In some embodiments, the method comprises mixing the purified proteins in proportions to generate the desired edible protein composition.

Gene Isolation and Preparation

Genes were selected from national gene sequence databases and specific genes were ordered from commercial suppliers. Genes sequences were confirmed at university labs. Genes with selected sequences were inserted into viral plasmids. The viral plasmids were inserted into yeast and/or *E. coli* bacteria utilizing standard protocols. Host colonies were developed and measured for protein expression levels. Colonies with highest yields were isolated and expanded in bioreactors. Proteins were extracted through centrifugation and processed via protocols specific to host organism.

Post Processing

Purified proteins were mixed in proportion by weight to re-create desired product (Egg white, others). When *Saccharomyces cerevisiae* was the host organism, in some applications, the expressed protein was not separated from host organism. In these instances, the colonies expressing different proteins themselves were mixed and deactivated by heat to create an edible host-expressed protein combination.

Ovotransferrin

Ovotransferrin was the first protein to be expressed due to its challenging structure. Ovotransferrin is has a very complex quarternary structure with eight disulfide bonds. Ovotransferrin structure was identified from the national gene database: http://www.nebi.nlm.nih.gov/gene/396241—Chromosome 9; NC_006096.3 (4096869.4107617, complement). http://www.nchi.nlm.nib.gov/nuccore/X02009.1 (mRNA sequence). Oligos were ordered from Integrated DNA technologies. PCR of the ovotransferrin oligo was performed. After an appropriately-sized fragment was obtained, gel was purified and cloned into TOPO pCR2.1. Several mini-preps of plasmid DNA were performed & followed by an EcoRI digestion. Agarose gel was performed and the expected sized band was obtained.

The sequence was inserted into *S. Cerevisiae* using the procedure described herein above. Optimization of *S. Cerevisiae* strains/colonies for protein production can be achieved by utilizing standard optimization procedures.

Application and Advantages

The compositions disclosed herein provide for means to create edible proteins from single-celled organisms which can be useful in providing a valuable source and supply of nutrition in areas with space and/or arable land constraints. The compositions and methods disclosed herein are especially advantageous as these use fewer resources than conventional poultry farming to create similar amounts of edible proteins. Further, the compositions and methods of making the compositions disclosed herein generate fewer waste products to form similar amounts of proteins as conventional poultry farming. The methods of making the compositions of the present disclosure use organisms with no known nervous system. Thus compositions of the present disclosure also circumvent animal cruelty issues. Lastly, the compositions and methods disclosed herein are particularly advantageous because these provide means for making an edible protein with customized amino acid content and accessory nutrients.

Additional Embodiments

Reference will now be made to more specific embodiments of the present disclosure and experimental results that provide support for such embodiments. However, Applicants note that the disclosure below is for illustrative purposes and is not intended to limit the scope of the claimed subject matter in any way.

Example 1 pPICZα-A-Ovotransferrin was linearized and transformed into host strain GS115 via electroporation. 5-10 positive clones have been selected and verified by PCR. One clone (Ovotransferrin-2) was chosen for cell culture. During 96 hours of induction by methanol, ovotransferrin appeared to be overexpressed and released into cell media examined by SDS PAGE.

1. Materials
   pPicZα-A plasmid (Life Tech); host strain DH5!, GS115 (Life Tech); Protein Marker (Creative BioMart); PVDF transfer membrane (Millipore); SUPER ECL PLUS (APPLYGEN); Acr, Bis, Tris (Sigma-Aldrich); SDS (Amresco); Tyrptone, Yeast Extract (OXOID); PCR tube (Fisher); 0.22" m sterile filter and dialysis bag (Millipore); Ni2+IDA (Zoonbio); Agarose (Creative BioMart); DNA/plasmids extraction Kits (AXYGEN); SAC I (NEB); Regular chemical reagents (Sigma Aldrich).
2. Recipe
   LB: Trypton 1%, Yeast Extract 0.5%, NaCl 1%, PH 7.0; Low salt LB: Trypton 1%, Yeast Extract 0.5%, NaCl 0.5%, PH 7.0, 1.5% agar (plate), adjust pH to 7.4 using NaOH YPD: Yeast Extract 1%, Trypton 2%, glucose 2%, agar 1.5% (plate) YPDS: Yeast Extract 1%, Trypton 2%, glucose 2%, 0.1 mol/L Sorbitol, agar 1.5% (plate) BMGY: Yeast extract 1%, Tryptone 2%, K Phosphate (pH6.0) 100 mM, YNB 1.34%, Biotin (4×10−5%), Glycerol 1% BMMY: Yeast extract 1%, Peptone 2%, K Phosphate (pH6.0) 100 mM, YNB 1.34%, Biotin (4×10−5%), methanol 0.5%
3. Instruments
   Primarily used. Allegra 21R (BECKMAN) Biological LP, Mini Protean II, Gel Doc2000 PTC-200 (MJ Research) 320-S pH (Mettler Toledo) AR5120 Scale (AHOM S) MultiTemp III water bath, Hofer MV-25 UV (Amersham Pharmacia) IceMaker (SANYO) JY92-2D Sonicator Gene Pulser Xcell (BioRad), NANODROP2000 (Thermo)

Example 2

Plasmid Extraction and Linearization
   Ovotransferrin plasmid was transformed into DH5α strain and amplified. The extraction of pPICAαA-Ovotransferrin plasmid is ~10" g, linearized by Sac I, DNA electrophoresis in agarose gel is shown in FIG. 1.

Example 3

Transformation of pPICZaA-Ovotransferrin into GS115
   10 μL linearized pPICZaA-Ovotransferrin were pipetted into 80 μL electrocompetent cells in a 1.5 mL Eppendorf tube, mixed well then transferred to a cuvette having a 0.2 cm gap. 310 μL of media was added and the tubes were prechilled for 5 minutes. Electroporation was performed at (1700 V, 8 ms, 2 electroshocks). 1 mL prechilled 1 M sorbitol was added into the cuvette, mixed using pipette and the sample transferred to 2 μL EP tube and, incubated at 30° C. for 2 hours. 50 μL, 100 μL and 200 μL cells were plated onto 100 μg/mL Zeocin YPD media and the plates were incubated at 30° C. for 48 hours. A single colony was picked up and grown in 10 mL YPD media (100 μg/mL Zeocin) at 30° C. overnight (180 rpm). Cell culture was streaked overnight onto YPD plates having 500 μg/mL, 1 mg/mL, and 2 mg/mL. The single colony (Zeocin) was picked up and grown in the same media overnight. Six positive clones were selected and marked as Ovotransferrin-1, Ovotransferrin-2, Ovotransferrin-3, Ovotransferrin-4, Ovotransferrin-5, Ovotransferrin-6. The clones were amplified by PCR using an AOX primer. The targeted gene should have a length of ~2.7 kpb.

Example 4

Ovotransferrin Expression
   Ovotransferrin-2 single colony was streaked into 9 mL YPD (Zeocin 200 μg/mL) and incubated at 30° C. for 24 hours (220 rpm). 350 μL was pipetted into 35 mL BMGY (Zeocin 200 μg/mL) and grown at 30° C. for 22 hours (220 rpm). The culture was centrifuged at 10,000 g for 2 minutes. Supernatant was poured off and cell pellets were collected. Yeast pellet was then re-suspended in 35 mL BMMY and 250 mL was transferred to a flask and grown at 30° C. for 24 hours (220 rpm). Next, the yeast pellet suspension was inducted by adding methanol for 96 hours. Methanol was added every 12 hours to keep methanol at 0.5% (v/v) in the flask. Culture media was sampled every 24 hours, centrifuged at 10,000 g for 2 minutes, and supernatant was collected and concentrated using PEG20000. The supernatant was then loaded onto an SDS PAGE.

Example 5

1. Overview
   Using the pPicZaA-RG008 plasmid as templates, the target gene sequence was amplified. The target gene was then sub-cloned into Expression Vector PYE-GAPa for expression. After verification by enzyme digestion and sequencing, 10 μg of PYE-GAPa-RG008 plasmid was digested. Each enzyme cuts once in the GAP promoter region to linearize the vector. The pichia GS115 was transformed. Positive clones were identified by PCR, and 10 strains of positive clones were obtained. A couple positive clones were chosen. Large scale expression can be carried out in shake flask or by fermentation. Expression condition was optimized. RG008-his protein is expressed into the medium. The analysis of the RG008 protein expression both from the cells and the medium was carried out though SDS-PAGE and WB.
2. Material
   pPicZα-A plasmid (Life Tech); host strain DH5α, GS115 (Life Tech); Protein Marker (Creative BioMart); PVDF transfer membrane (Millipore); SUPER ECL PLUS (APPLYGEN); Acr, Bis, Tris (Sigma-Aldrich); SDS (Amresco); Tyrptone, Yeast Extract (OXOID); PCR tube (Fisher); 0.22 μm sterile filter and dialysis bag (Millipore); Ni2+IDA (Creative BioMart); Agarose (Creative BioMart); DNA/plasmids extraction Kits (AXYGEN); SAC I (NEB); and Regular chemical reagents (Sigma Aldrich).
3. Recipe:
   LB medium: peptone 1%, Yeast Extract 0.5%, NaCl 1%, agar 1.5%, NaOH pH 7.4.
   Low-Salt LB medium: peptone 1%, Yeast Extract 0.5%, NaCl 0.5%, agar 1.5%, NaOH pH 7.4.
   YPD medium: peptone 2%, Yeast Extract 1%, dextrose (D-glucose), agar 1.5%.

YPDS medium: peptone 2%, Yeast Extract 1%, dextrose (D-glucose), 0.1 mol/L Sorbitol, agar 1.5%.

4. Instruments Primarily Used.

Allegra 21R (BECKMAN); Biological LP, Mini Protean II, Gel Doc2000 PTC-200 (MJ Research); 320-S pH (Mettler Toledo) AR5120 Scale (AHOM S); MultiTemp III water bath, Hofer MV-25 UV (Amersham Pharmacia) IceMaker (SANYO); JY92-2D Sonicator; Gene Pulser Xcell (Bio-Rad); and NANODROP2000 (Thermo).

5. Description of Experimental Procedure 5.1 PYE-GAPa-RG008 Vector Construction

The target gene sequence was amplified. The target fragment of RG008 was sub-cloned into EcoR I and Not I sites of Expression Vector PYE-GAPa.

5.2 Transformation of PYE-GAPa-RG008 into GS115

10 μL linearized PYE-GAPa-RG008 was pipetted into 80 μL electrocompetent cells in a 1.5 mL EP tube. The cells were mixed well and then transferred to a cuvette having a 0.2 cm gap. 310 μL media were then added and the preparation was prechilled for 5 minutes.

Electroporation (1700V, 8 ms, 2 electroshocks) was then performed. 1 mL of prechilled 1M sorbitol was added into the cuvette and mixed using a pipette to transfer the sample to a 2 mL EP tube. The preparation was then incubated at 30° C. for 2 hours. 50 μL, 100 μL and 200 μL cell preparations were then plated onto 100 μg/mL Zeocin YPD media. The plated preparations were then incubated at 30° C. for 48 hours, after which a single colony was picked up and then grown in 10 mL YPD media (100 μg/mL Zeocin) at 30° C. overnight (180 rpm). A cell culture was then streaked overnight onto YPD plates having 500 μg/mL, 1 mg/mL, 2 mg/mL Zeocin. The single colony was picked up and grown in the same media overnight.

5.3 Positive Clones Identification

Six colonies were selected from the YPD plates and genome DNA was extracted. When amplified by PCR using an AOX1 primer, the target gene should have the length of ~2.6 kb.

5.4 Western Blot Analysis (Supernatant)

Western Blot Identification using Mouse-Anti-His antibody was performed. Expression assessment showed that there was no secrete expression of PYE-GAPa-RG008 protein (~79 kDa) in culture supernatant.

5.5 Intracellular Expression Testing

A single colony was streaked into 10 mL YPD and incubated at 30° C. overnight (250 rpm). 0.1 mL was then pipetted into 50 mL YPD and grown at 30° C. for 22 hours (250 rpm). 1 ml of the cell culture was transferred into a 1.5-ml microcentrifuge tube every hour. These samples were used to analyze expression levels and determine an optimal time to harvest. The samples were centrifuged at maximum speed in a table top microcentrifuge for 2-3 minutes at room temperature and then poured off supernatant, collected as cell pellet, and frozen quickly in liquid nitrogen. The cells pellets were then stored at −80° C. until ready to assay.

5.6 Protein Purification by Ni-Affinity Column (Intracellular)

Cell paste harvest from 800 ml Gs115 culture was resuspended in 50 ml Buffer A (20 mM Tris-HCl containing 500 mM NaCl, pH 8.0). Ultrasonic breaking of cells was performed with protease inhibitors on ice and centrifuged at 12,000 rpm for 15 minutes. The supernatant was then collected and loaded onto Ni-NTA column pre-equilibrated by lysis buffer. The column was washed by a 10 column volume of lysis buffer B, containing 20 mM Tris-HCl, 20 mM imidazole, 150 mM NaCl. The target proteins were eluted by buffer C (20 mM Tris-HCl buffer, pH 8.0, containing 150 mM NaCl, and 250 mM imidazole). After purification, the target protein was transferred into a dialysis bag and loaded onto SDS PAGE.

5.7 Western Blot Analysis (Intracellular)

Using Mouse-Anti-His antibody, one band showed an apparent molecular weight of 70 kDa. The target protein then needed to be verified by the RG008 specify antibody.

Example 6

1. Overview pPICZa-A-Ovotransferrin was linearized and transformed into host strain GS115 via electroporation. 5-10 positive clones were selected and verified by PCR. One clone, Ovotransferrin-2, was chose for cell culture. During 96 hours induction by methanol, ovotransferrin appears to be overexpressed and released into cell media examined by SDS PAGE.

2. Material pPicZa-A plasmid (Life Tech); host strain DH5a, GS115 (Life Tech); Protein Marker (Creative BioMart); PVDF transfer membrane (Millipore); SUPER ECL PLUS (APPLYGEN); Acr, Bis, Tris (Sigma-Aldrich); SDS (Amresco); Tyrptone, Yeast Extract (OXOID); PCR tube (Fisher); 0.22 m sterile filter and dialysis bag (Millipore); Ni2+IDA (Zoonbio); Agarose (Creative BioMart); DNA plasmids extraction Kits (AXYGEN); SAC I (NEB); and Regular chemical reagents (Sigma Aldrich).

3. Recipe

LB: Trypton 1%, Yeast Extract 0.5%, NaCl 1%, PH 7.0; Low salt LB: Trypton 1%, Yeast Extract 0.5%, NaCl 0.5%, PH 7.0, 1.5% agar (plate), adjust pH to 7.4 using NaOH YPD: Yeast Extract 1%, Trypton 2%, glucose 2%, agar 1.5% (plate); YPDS: Yeast Extract 1%, Trypton 2%, glucose 2%, 0.1 mol L Sorbitol, agar 1.5% (plate); and BMGY: Yeast extract 1%, Tryptone 2%, K Phosphate (pH6.0) 100 mM, YNB 1.34%, Biotin (4×10−5%), Glycerol 1% BMMY: Yeast extract 1%, Peptone 2%, K Phosphate (pH6.0) 100 mM, YNB 1.34%, Biotin (4×10−5%), methanol 0.5%.

4. Instruments

Primarily used: Allegra 21R (BECKMAN); Biological LP, Mini Protean II, Gel Doc2000 PTC-200 (MJ Research); 320-S pH (Mettler Toledo) AR5120 Scale (AHOM S) MultiTemp III water bath, Hofer MV-25 UV (Amersham Pharmacia) IceMaker (SANYO) JY92-2D Sonicator; and Gene Pulser Xcell (BioRad) NANODROP2000 (Thermo).

5. Description of Experimental Procedure 5.1. Plasmid Extraction and Linearization Ovotransferrin plasmid was transformed into DH5a strain and amplified. The extraction of pPICAaA-Ovotransferrin plasmid is −10 g, linearized by Sac I, DNA electrophoresis in agarose gel.

5.2. Transformation of pPICZaA-Ovotransferrin into GS115

10 μL of linearized pPICZaA-Ovotransferrin was pipetted into 80 μL of electrocompetent cells in a 1.5 mL EP tube and mixed well. The mixture was then transfered to a cuvette having a 0.2 cm gap, and then 310 μL of media was added to the mixture, which was prechilled for 5 minutes. Electroporation was then performed (1700V, 8 ms, 2 electroshocks). 1 mL of prechilled 1 M sorbitol was added into the cuvette, mixed using pipette transfer of the sample to a 2 mL EP tube, and incubated at 30° C. for 2 hours. 50 μL, 100 μL, and 200 μL cells were plated onto 100 μg/mL Zeocin YPD media. The plates were incubated at 30° C. for 48 hours. Next, a single colony was picked up and grown in 10 mL YPD media (100 μg/mL Zeocin) at 30° C. overnight (180 rpm). A cell culture was streaked overnight onto YPD plates having 500 µg/mL, 1 mg/mL, 2 mg/mL Zeocin. The single colony was picked up and grown in the same media overnight. Six positive clones were selected and marked as Ovotransferrin-1, Ovotransferrin-2, Ovotransferrin-3, Ovotransferrin-4, Ovotransferrin-5, Ovotransferrin-6. When amplified by PCR using an AOX primer, the target gene should have the length of ~2.7 kpb.

5.3. Ovotransferrin Expression

Ovotransferrin-2 single colony was streaked into 9 mL YPD (Zeocin 200 µg/mL), incubated at 30° C. for 24 hours (220 rpm), 350 µL of the mixture was pipetted into 35 mL BMGY (Zeocin 200 µg/mL), and grown at 30° C. for 22 hours (220 rpm). The culture was centrifuged at 10,000 g for 2 min, after which supernatant was poured off and cell pellets were collected. A yeast pellet was re-suspended in a 35 mL BMMY, transferred to a 250 mL flask, grown at 30° C. for 24 hours (220 rpm), and inductioned by adding methanol for 96 hours. Methanol was added every 12 hours to keep methanol of 0.5% (v/v) in the flask. Culture media was sampled every 24 hours, centrifuged at 10,000 g for 2 minutes, and supernatant was collected. The supernatant was concentrated using PEG20000 and then loaded onto SDS PAGE.

What is claimed is:

1. An avian-free egg white substitute composition, the composition comprising:
    a plurality of genetically modified micro-organisms, wherein the genetically modified micro-organisms express a plurality of different proteins selected from the group consisting of Ovalbumin, Ovotransferrin, Ovoglobulin G2, Ovoglobulin G3, Ovomucin, Lysozyme, Ovoinhibitor, Ovoglycoprotein, Flavoprotein, Ovomacroglobulin, Avidin, Ovomucoid, and Cystatin; and
    wherein at least some of the plurality of different proteins remain within the genetically modified micro-organisms.

2. The composition of claim 1, wherein the plurality of different proteins comprise Ovomucoid.

3. The composition of claim 1, further comprising a flavor enhancer.

4. The composition of claim 3, wherein the flavor enhancer is yeast.

5. The composition of claim 1, further comprising a calcium supplement.

6. The composition of claim 1, further comprising added vitamins.

7. The composition of claim 1, further comprising a gelling agent.

8. The composition of claim 1, further comprising algal omega-3 fatty acids.

9. The composition of claim 1, wherein the plurality of different proteins comprise Ovalbumin, Ovotransferrin, Ovoglobulin G2, Ovoglobulin G3, Ovomucin, Lysozyme, Ovoinhibitor, Ovoglycoprotein, Flavoprotein, Ovomacroglobulin, Avidin, and Cystatin.

10. The composition of claim 9, wherein the plurality of different proteins further comprise Ovomucoid.

11. The composition of claim 1, wherein the genetically modified micro-organisms are in the form of edible yeast.

12. A method of making an avian-free egg white substitute, the method comprising:
    expressing genes in a plurality of, genetically modified micro-organisms, wherein the genes encode a plurality of different proteins selected from the group consisting of Ovalbumin, Ovotransferrin, Ovomucoid, Ovoglobulin G2, Ovoglobulin G3, Ovomucin, Lysozyme, Ovoinhibitor, Ovoglycoprotein, Flavoprotein, Ovomacroglobulin, Avidin, Ovomucoid, and Cystatin,
    wherein at least some of the plurality of different proteins remain within the genetically modified micro-organisms; and
    combining the genetically modified micro-organisms to form the avian-free egg white substitute.

13. The method of claim 12, wherein the genetically modified micro-organisms comprise multiple yeast colonies.

14. The method of claim 13, wherein each yeast colony of the multiple yeast colonies expresses a protein selected from the group comprising: Ovalbumin, Ovotransferrin, Ovomucoid, Ovoglobulin G2, Ovoglobulin G3, Ovomucin, Lysozyme, Ovoinhibitor, Ovoglycoprotein, Flavoprotein, Ovomacroglobulin, Avidin, and Cystatin.

15. The method of claim 13, wherein the yeast is *Saccharomyces cervevisiae*.

16. The method of claim 15, wherein the yeast is *Picchia pastoris*.

17. The method of claim 12, wherein the genetically modified micro-organisms are bacteria.

18. The method of claim 17, wherein the bacteria is *E. coli*.

19. The method of claim 12, wherein the avian-free egg white substitute further comprises a gelling agent.

20. The method of claim 12, further comprising: expanding the genetically modified cells; and expressing each of the aforementioned proteins in bioreactors.

21. The composition of claim 1, wherein the genetically modified micro-organisms comprise multiple yeast colonies.

22. The composition of claim 1, wherein the genetically modified micro-organisms comprise bacteria.

* * * * *